United States Patent [19]
Littig

[11] Patent Number: 5,746,773
[45] Date of Patent: May 5, 1998

[54] C-SHAPED SPRING MEMBER FOR PROSTHETIC LIMBS

[75] Inventor: David H. Littig, Ventura, Calif.

[73] Assignee: United States Manufacturing Company, Pasadena, Calif.

[21] Appl. No.: 615,026

[22] Filed: Mar. 13, 1996

[51] Int. Cl.$^6$ .................................. A61F 2/62; A61F 2/66
[52] U.S. Cl. ........................... 623/35; 623/38; 623/46; 623/52
[58] Field of Search ........................ 623/38, 35, 52, 623/50, 53, 55, 47, 44, 46, 39

[56] References Cited

U.S. PATENT DOCUMENTS

| | | | |
|---|---|---|---|
| 57,691 | 9/1866 | Drake | 623/52 X |
| 597,465 | 1/1898 | Hagen | 623/53 X |
| 622,140 | 3/1899 | Ginn | 623/35 |
| 1,552,869 | 9/1925 | Nevin | 623/52 |
| 2,443,356 | 6/1948 | Mathis | 623/54 X |
| 2,453,969 | 11/1948 | Carter | 623/53 X |
| 3,723,997 | 4/1973 | Kolman | 623/46 X |
| 4,547,913 | 10/1985 | Phillips | 623/27 |
| 4,645,509 | 2/1987 | Poggi et al. | 623/55 |
| 5,156,632 | 10/1992 | Wellershaus | 623/55 |
| 5,376,137 | 12/1994 | Shorter et al. | 623/44 |
| 5,376,139 | 12/1994 | Pitkin | 623/51 |
| 5,458,656 | 10/1995 | Phillips | 623/27 |

FOREIGN PATENT DOCUMENTS

| | | | |
|---|---|---|---|
| 2698538 | 6/1994 | France | 623/55 |
| 4037928 | 5/1992 | Germany | 623/55 |
| 9410942 | 5/1994 | WIPO | 623/53 |

OTHER PUBLICATIONS

O & P Business News, Mar. 1, 1996, *M+ Introducing the Seattle C Stance©*, pp. Cover and 21.

*Primary Examiner*—David H. Willse
*Attorney, Agent, or Firm*—Christie, Parker & Hale, LLP

[57] ABSTRACT

A stance phase flexion device for a prosthesis comprises a composite C-shaped spring member formed from a plurality of thermoset synthetic resin-impregnated high strength carbon filament sheets molded together in a compression mold. The spring member includes a standard hole pattern located in an upper leg of the spring and a standard hole pattern on the lower leg of the spring, for connecting the spring between adjacent prosthetic components for simulating normal flexion between the adjacent components. The C-shaped member is normally rigid in a rest position maintaining its C-shaped configuration. The C-shaped member has spaced apart upper and lower legs that elastically flex with energy absorbing compliance under a load tending to move the upper and lower legs together. The C-shaped member essentially resists elastic flexion in lateral directions and resists torsion loads.

4 Claims, 3 Drawing Sheets

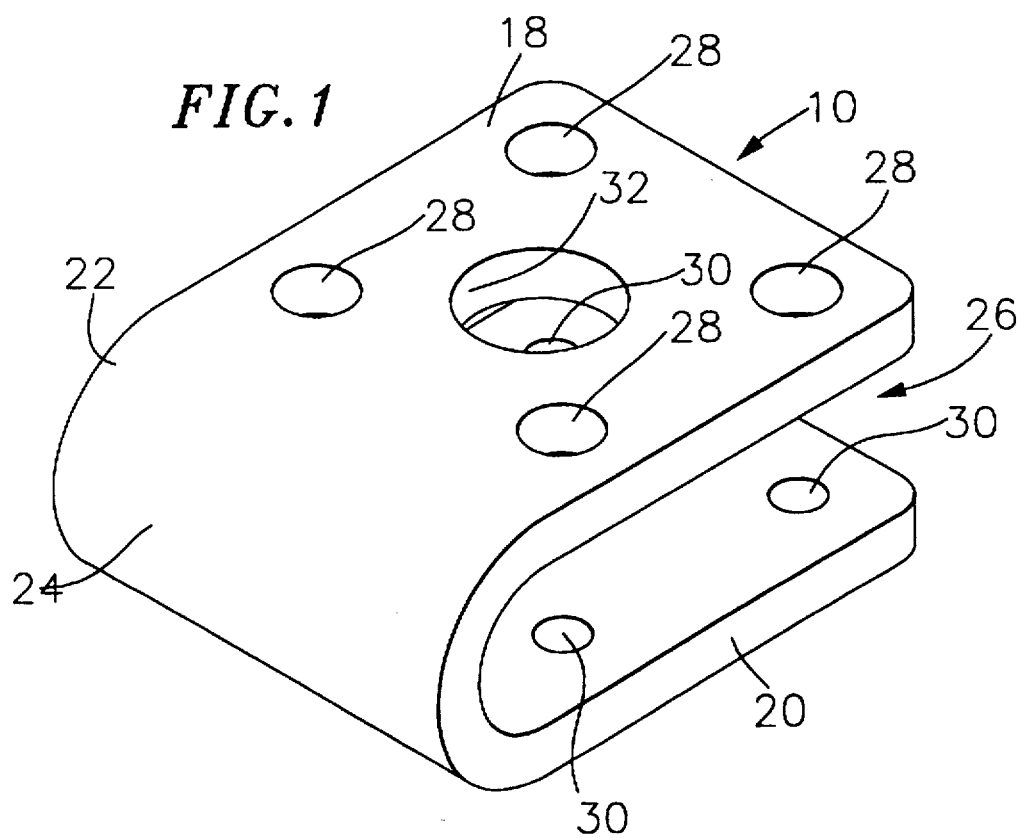
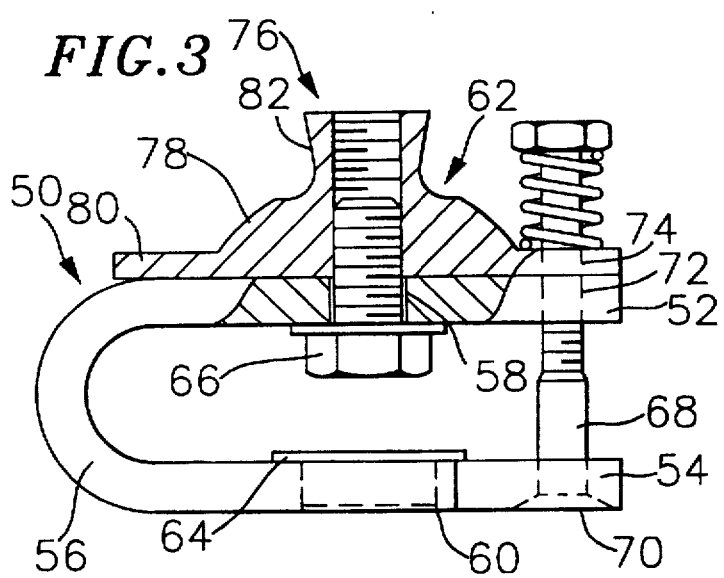

5,746,773

1

C-SHAPED SPRING MEMBER FOR PROSTHETIC LIMBS

FIELD OF THE INVENTION

This invention relates generally to prosthetic devices, and more particularly, to a stance phase flexion device comprising a C-shaped spring member positioned within a prosthesis for simulating flexion between prosthetic components and for absorbing shock on the prosthesis during walking or standing.

BACKGROUND OF THE INVENTION

In the course of walking, individuals use their muscles to provide the energy to raise and lower the torso with each stride. The amount of energy consumed depends upon the weight of the body and the range traveled. In normal individuals, the center of gravity of the body on average will rise and fall about 2 to 2.5 centimeters during one gait cycle in straight level walking.

Similarly, lateral deviation of the center of gravity of an equal magnitude will occur, and together these vertical and lateral displacements will describe a smooth double sinusoidal path with the body's center of gravity. A lower limb amputee using a prosthesis, however, experiences a greater than normal center of gravity rise and fall accompanied by a relative increase in energy consumption. Clinical data show that energy consumption rises also with the level of amputation as more joints and body segments are replaced with mechanical substitutes. Consequently, the loss of ankle, knee, and hip joints and connecting skeletal segments results in the loss of several of the major contributors to the smooth and energy-conserving control of the rise and fall of the body's center of gravity. Therefore, a prosthetic system which replaces or simulates replacement of the function of any of the lost gait determinants benefits the user through reduced energy costs.

One of the major contributors to an energy efficient gait in the non-amputee is known as knee flexion in stance. By flexing the knee during weight bearing, a non-amputee is limiting the rise of his center of gravity thus conserving energy with each gait cycle. The above knee amputee using currently available prosthetic systems cannot normally limit his center of gravity rise through knee flexion during weight bearing. Otherwise the knee will buckle and the amputee will fall.

Prior above-knee prostheses or prosthetic devices have been designed to accommodate knee flexion in the stance phase by including a mechanical hinge and a rubber block positioned above the knee segment. A problem with this prior design is that the mechanical hinge has been integrally designed in a knee segment of a prosthesis and is rigidly fixed with respect to the mechanical axis of the knee. Consequently its effectiveness cannot be optimized by sliding it fore and aft to alter its stability and "feel" to the amputee. In addition, a rigid mechanical hinge assembly is considerably more complicated and expensive to manufacture, as well as adding to the overall weight of the prosthesis.

Consequently, there exists a need for a new and improved stance phase flexion device for a lower limb prosthesis that can be universally used for all lower limb leg prosthetic components, is lightweight, long-lasting, and is easy and inexpensive to manufacture.

SUMMARY OF THE INVENTION

The present invention provides a stance phase flexion device for lower limb prosthetic application which eliminates the problems of prior existing flexion devices and is lightweight, universally adaptable for all leg prosthetic components, and is easy and inexpensive to manufacture.

In one embodiment, the stance flexion device comprises a generally C-shaped spring member positioned in an above-knee prosthesis between a thigh component and a knee component. The C-shaped spring member simulates knee joint flexion for the amputee which is typical for all individuals. The C-shaped spring member thereby prevents the center of gravity of the body from rising too high during walking, keeping the center of gravity smoother and flatter and conserving energy of the amputee.

Most above-knee prosthetic components are designed with standard hole patterns for connecting individual components. Consequently the C-shaped spring member includes standard hole patterns in its upper and lower surfaces such that the spring member can be universally mounted between prosthetic components of any manufacturer.

One process for making the C-shaped spring member includes forming a reinforced plastic spring member from a number of layers of synthetic resin-impregnated carbon graphite sheets molded under heat and pressure in a compression mold. The spring member is essentially rigid in its rest position, maintaining its generally C-shaped form, providing an open space at one end between the top and bottom legs of the C. The spring member has sufficient resilience during weight bearing to compress (reducing the space at the end of the C) and to resiliently flex in the opposite direction to a return position (enlarging the space at the end of the C) when weight bearing is released. The flexing motion of the C-shaped member is spring-like in assisting controlled spring-biased travel both under weight bearing and when the weight is released. The spring member can be manufactured having varying degrees of flexibility by aligning the fibers of individual sheets at angles to one another during the molding process. The specific stiffness of the hinge during use is a controlled factor dependent upon overall prosthesis length and weight of the user. Besides simulating knee flexion in the stance phase, the C-shaped spring member also absorbs shock on the prosthesis generated during a normal walking gait, thereby softening the attachment of the thigh component to the knee component in the prosthesis.

In a second embodiment of the invention, the C-shaped spring member is utilized in a below-knee prosthesis. In this embodiment, the upper leg of the spring member includes a centrally located hole for connection to a prosthetic link such as a frustoconical connector. An axially aligned hole is located in the lower leg of the spring member for receiving a fastener such as a T-nut which secures the spring to a foot prosthesis. The frustoconical connector then attaches to a lower leg component. The spring member in this embodiment also includes a gradual spring-loaded stop position at an open end of the spring for controlling the bending moment of the spring member. The spring member is positioned in the heel portion of a prosthetic foot for absorbing shock on the foot prosthesis generated during walking.

These and other aspects of the invention will be more fully described in the following detailed description and the accompanying drawings.

BRIEF DESCRIPTION OF THE DRAWINGS

FIG. 1 is a perspective view showing one embodiment of a C-shaped spring member of the present invention;

FIG. 3 is a side elevational view, partly in cross section, showing an alternative embodiment of the spring member of FIG. 1.

DETAILED DESCRIPTION

Figure 2:
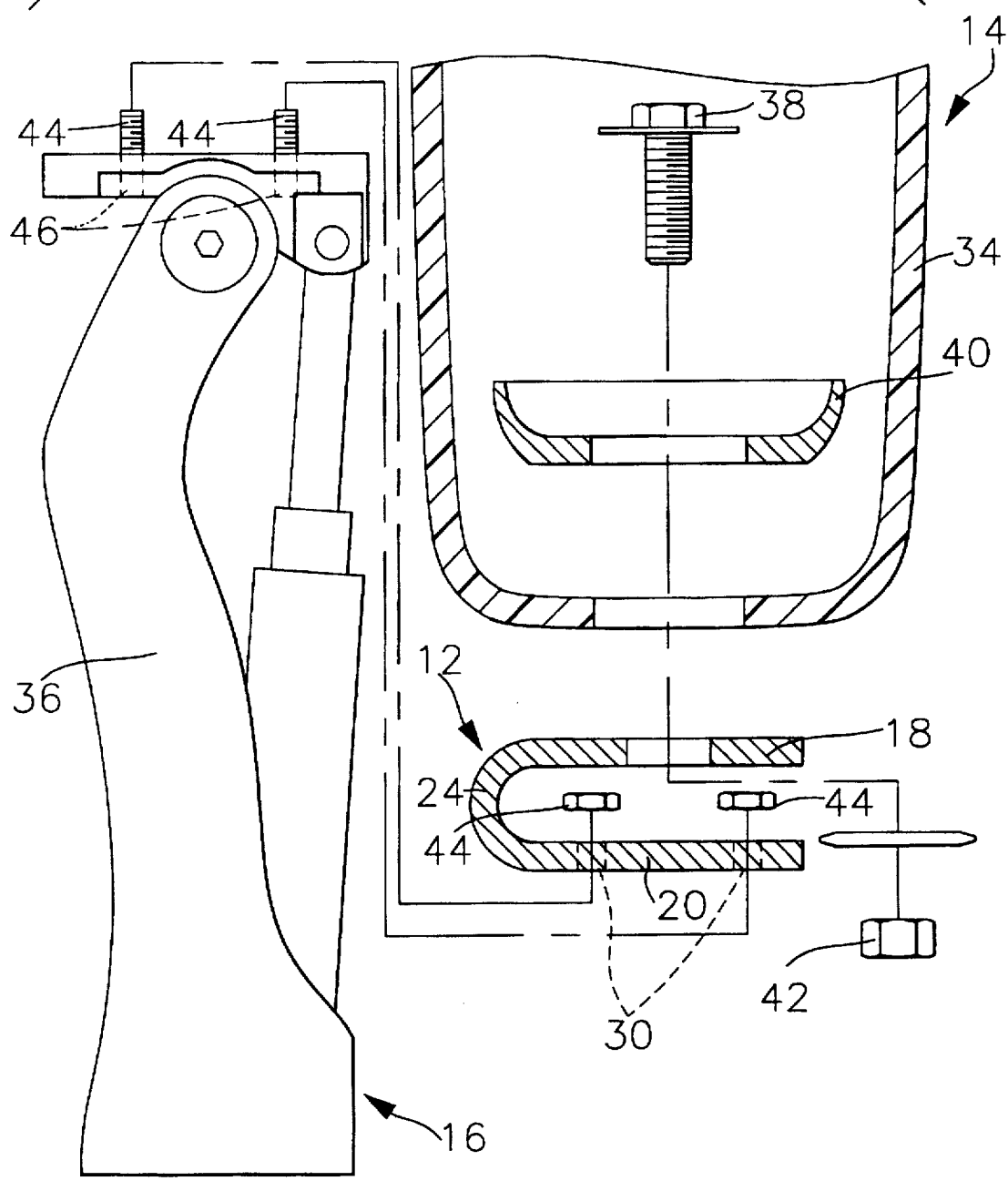
FIG. 2 is an exploded side elevational view, partly in cross section, showing the spring member of FIG. 1 incorporated into an above-knee prosthesis.

FIG. 1 shows a perspective view of a stance phase flexion device 10 of the present invention. The device is made from a high strength epoxy resin-impregnated carbon filament structure that is capable of elastically flexing under the weight of an amputee. As also shown in FIG. 2, the device is a generally C-shaped spring member 12 which in use is rigidly secured between adjacent prosthetic components 14 and 16. The spring member 12 includes a generally planar upper leg 18 spaced above and extending essentially parallel to a generally planar lower leg 20. Upper leg 18 and lower leg 20 are integrally formed as a one-piece unit at a front section 22 of the spring by a curved portion 24. Upper leg 18 and lower leg 20 terminate at an end opposite from the front section 22 to form an opening 26 between the ends of the upper and lower legs. The C-shaped member is of uniform thickness from end to end, and the upper and lower legs are essentially the same length. The distance between the upper and lower legs is in the range of about two to about four times the thickness of each leg.

The spring member is sufficiently rigid in the rest position to maintain its essentially C-shaped configuration. The spring member flexes resiliently to provide controlled energy-absorbing compliance under applied weight bearing tending to reduce the spacing between the upper and lower legs. The C-shaped member is essentially rigid (resistant to flexion) in lateral directions transverse to the axes of the upper and lower legs. The spring member also is resistant to torsion loads applied to the upper and lower legs of the C.

The preferred method of fabrication of the spring 12 is to use a plurality of synthetic resin-impregnated high strength filament sheets molded together in a compression mold. The sheets are arranged in the mold such that the filaments of adjacent sheets run at angles with respect to each other. For instance, an initial sheet is placed in the mold such that the filaments run horizontally in the mold, and successive sheets are placed in the mold such that the filaments extend at an angle with respect to the orientation of the filaments of the previous sheet. For example, the sheets are typically arranged at 30, 45, 60, or 90 degree angles with respect to previous sheets. By arranging the sheets in this fashion, the filaments are bound together and are prevented from separating under applied loads. Excellent results have been found experimentally using sheets of carbon filaments with an epoxy binder, commercially available from Cape Composites in San Diego, Calif. marketed as part number 63910.

The high strength resin-impregnated filament structure of the spring member, coupled with the specific geometry of individual prosthetic components, provides substantial compliances in the spring member with respect to certain specific types of loads, and more particularly, non-dissipative compliances, so that the energy put into the spring member during deflection (reducing of the space between the upper and lower legs) is returned by the spring member as the deflection force is removed. The spring member provides both a strong cushioning effect and energy storage in response to weight bearing loads on the respective portions of the prosthetic device. The rigidity of the C-shaped member also provides controlled spring-biased resistance to weight bearing as the C-shaped member closes during weight bearing. Spring member 12 is purposely formed as a C-shaped structure to provide the proper configuration in the filament reinforced structure for controlled compliance during load carrying. Specific load requirements can be achieved by making the spring member thinner so that the deflection rate of the spring is lower, though the compliance which may be obtained in this manner alone appears limited because of the increase in stress and corresponding reduction in load carrying capacity associated with more compliant structures. The exact thickness of the spring member directly correlates to the amount of weight to be placed on the prosthesis.

The C-shaped spring member 12 includes a standard pattern of attachment holes 28 passing through the upper leg 18, and an axially aligned standard pattern of holes 30 passing through the lower leg 20. The standard pattern of holes 28 include four ³⁄₁₆-inch holes, one located in each corner of the upper section 18. The size and spacing of the holes mirrors the standard hole pattern on individual prosthetic components. Similarly, standard hole pattern 30 comprises four ¼-inch holes, one located in each corner of lower section 20. Hole pattern 30 also is sized and positioned to communicate with the standard hole patterns on prosthetic components.

Upper leg 18 also includes a larger centrally located hole 32 for alternative attachment of a prosthetic component. Hole 32 preferably is ¾-inch diameter hole positioned in the middle of the upper leg 18. Lower leg 20 could also include one larger centrally located hole (not shown) for attachment to a prosthetic component, if desired. By using these large holes and a single bolt attachment, the device may be translated fore or aft with respect to the attaching components thus optimizing its "feel" and the stability of the prosthesis.

As shown in FIG. 2, C-shaped spring member 12 preferably is incorporated into an above-knee prosthesis between a thigh component 34 and a knee component 36. The spring member 12 is rigidly secured to the thigh component by a screw 38 which passes through hole 32 and into a dish 40 positioned in the thigh component. A lock nut 42 is threaded on the end of the screw 38 to secure the thigh component to the upper section of the spring member. Dish 40 includes a slotted hole through which screw 38 passes for adjustably aligning the thigh component 34 to the spring member. Alternatively, the thigh component could be secured to the spring by four screws passing through holes 28 and into four axially aligned holes in the dish 40.

Knee component 36 is attached to the lower section 20 of the spring member 12 by four screws 44 which pass through holes 30 and into axially aligned threaded holes 46 in the knee component 36. Alternatively, the knee component 36 could be attached to the lower section 20 through the use of a screw and a centrally located hole as shown with respect to the upper section and thigh component.

Most standard thigh and knee components can be utilized with the C-shaped spring member because the hole patterns are universally adopted within the prosthetics industry. Knee component 36 shown is a hydraulic knee unit, however, other known knee units such a pneumatically or mechanically operated units are also suitable for use with the C-shaped spring. The spring member in the configurations shown in FIG. 2 simulates knee flexion typical for an above knee amputee. The spring member allows the prosthesis to assume the normally bent position in the stance phase. The spring member furthermore allows the amputee to minimize his center of gravity rise during walking, thereby conserving energy of the amputee. The spring member also absorbs shock placed on the prosthesis by the amputee during walking.

Figure 4:
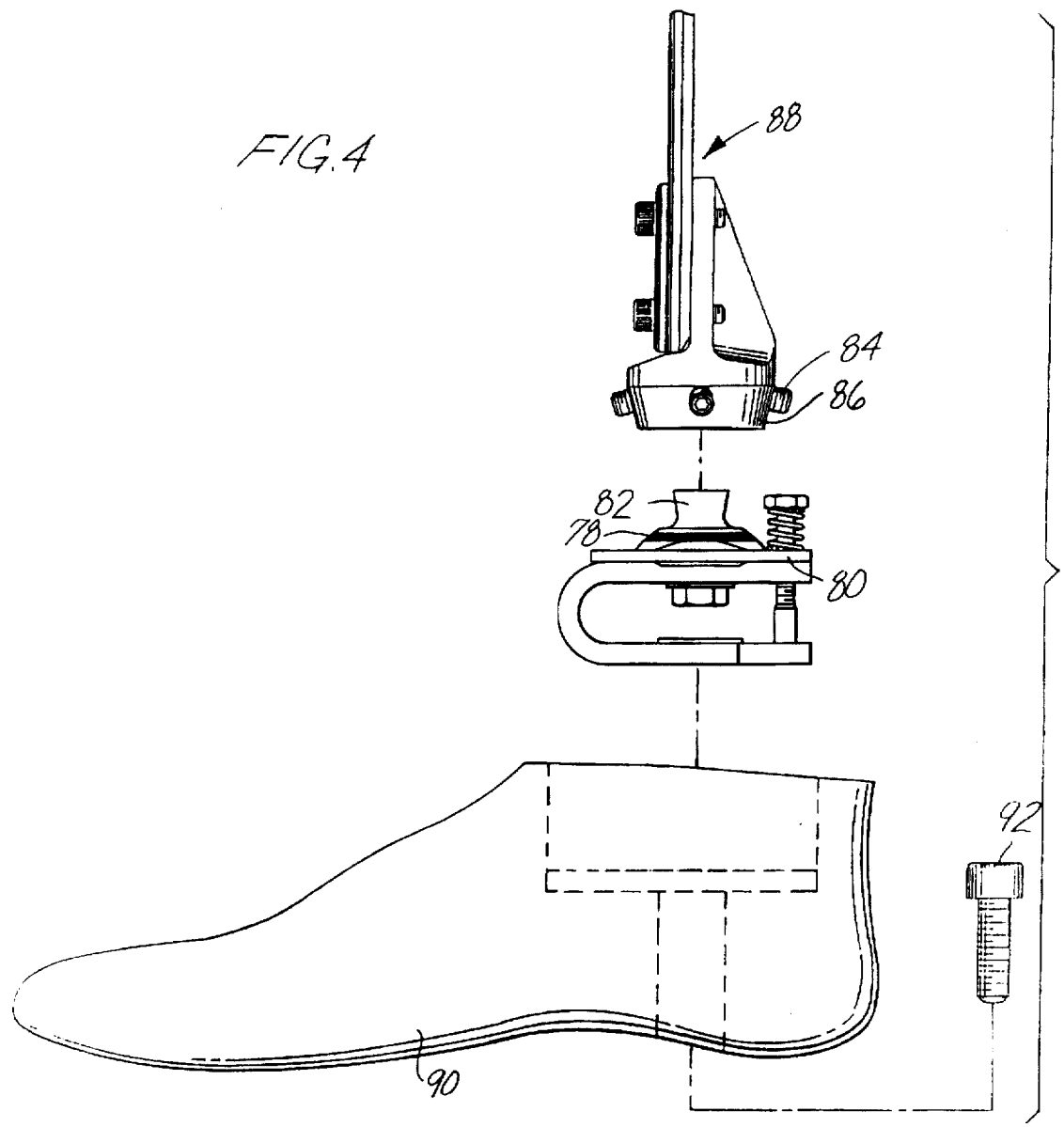
FIG. 4 is an exploded side elevational view of the spring member of FIG. 3 incorporated into a below-knee prosthesis.

FIGS. 3 and 4 illustrate an alternative C-shaped spring member 50 for use in a lower leg prosthesis for below knee amputations. Spring member 50 includes a generally planar upper leg 52 and an axially aligned and parallel spaced substantially planar lower leg 54. Upper leg 52 and lower leg 54 are integrally connected by a curved front section 56. Spring member 50 also is made from a high strength resin-impregnated filament structure formed in layers through a compression mold similar to that of spring member 12.

Spring member 50 includes a centrally located hole 58 in the upper leg 52 and a corresponding centrally located and axially aligned hole 60 in the lower leg 54. Hole 58 is for the rigid attachment of prosthetic link 62, and hole 60 is for a threaded T-nut 60. Link 62 is rigidly secured to the upper leg 52 by a screw 66 which passes through hole 58. Located at the ends of spring member 50 opposite from the curved section 56 is a spring biased stop screw 68. Stop screw 68 passes through holes 70 and 72 through lower section 54 and upper section 52, respectively, and through hole 74 located in link 62.

Prosthetic link 62 includes a male connector 76 having a spherically convex base 78 rigid with a generally flat plate 80 that provides a connector portion for connection to an adjacent prosthetic component. A central boss 82 of frustopyramidal configuration projects away from the spherically convex base. The frustopyramid formed by the main portion of the boss is of square cross section and has four uniform sides facing angularly upwardly and outwardly in four directions spaced apart by 90 degrees. The four angular sides of the boss are contacted by separate set screws 84, see FIG. 4, which are carried at 90 degree intervals spaced apart around the bottom portion of a female socket 86.

In use, male connector 76 can be inserted into the socket 86, and the set screws can be loosened or tightened and the male connector moved into various angular configurations for providing angular adjustments between the C-shaped spring member and a lower leg component 88. The C-shaped member is also connected to a foot component 90 and rigidly secured thereto by a screw 92 which is threaded into the T-nut 64.

Spring member 50 simulates ankle flexion as well as absorbing energy placed on the lower leg prosthesis during walking. The spring flexes to absorb the energy and returns to its unstressed position as the weight is removed from the spring. The stop screw 68 prevents the spring from opening as the weight is removed from the lower leg prosthesis. Alternatively, a dacron web strap inhibitor can be substituted for the stop screw to perform the same function. A dacron web strap could also be utilized for spring 12, in applications where opening of the spring occurs.

EXAMPLE

An experimental C-shaped spring member designed for normal activity for an above knee prosthesis for an individual weighing up to 185 pounds was fabricated as follows. The spring member was made of a thermoset plastic material comprising sheets of prepregnated carbon filaments with a 350° F. set point epoxy resin. The filaments in each sheet run essentially parallel to each other. The material is purchased in the form of a 725foot roll, 12-inch wide and 6 mil thick and is stored at 24/22° F. until used. The carbon epoxy prepregnated sheet material is first left at ambient temperature to warm up to 70/50° F. prior to cutting. The material is then cut into a rectangular laminate, 1.75-inch×6.5-inch, at 45° orientation with the original fibers. Each rectangular laminate is laid up on another to form a +/− 45° laminate. Twenty-one laminates are stacked at a 45° angle with respect to a previous laminate to form the center core of the component. The center laminate is then covered by 90° laminates on both sides. The lay up is then placed inside of a cold mold having a C-shaped configuration.

The component is manufactured by compression molding wherein the initial layup temperature is 80/65° F. The platen start temperature is 125/100° F. which is raised during the molding process to 315° F. The applied pressure on the laminate is 200/150 psi at 250° F. The molding process is held at 350° F. under 200/150 PSI for one hour. The spring member is then held in a cool down and post cure period for two hours at 95/85° F. before being demolded and deburred at room temperature. The resulting dimensions of the C-shaped member include a thickness for each the upper and lower legs of 0.28 inch with an overall height from the upper surface of the upper leg to the lower surface of the lower leg being 1.3 inches. The curved portion connecting the upper leg and the lower leg has an outside radius of 0.65 inch and an inside radius of 0.38 inch.

What is claimed is:

1. An above-knee prosthesis comprising:

a prosthetic thigh component;

a prosthetic knee component; and a modular composite generally C-shaped spring member formed from a plurality of synthetic resin-impregnated high strength filament sheets molded together as a one-piece unit, the C-shaped member being normally rigid in a rest position maintaining its C-shaped configuration, the C-shaped member having spaced apart upper and lower legs that elastically flex with energy absorbing compliance under a load tending to move the upper and lower legs together, while the C-shaped member essentially resists elastic flexion in lateral directions, the spring member including means for being rigidly secured between the thigh component and the knee component along a weight-bearing axis of the above knee prosthesis for simulating flexion between the thigh component and the knee component and providing a main weight-bearing compliance for the prosthesis in which the securing means includes a pattern of holes extending through the upper and lower legs of the spring member and releasable fastening means engaged with the pattern of holes for providing alignment movement of the C-shaped member fore and aft of the weight-bearing axis.

2. The prosthesis of claim 1 wherein the means for securing the spring between the thigh component and the knee component includes a centrally located hole passing through the upper leg of the spring member and a centrally located hole passing through the lower leg of the spring member.

3. The prosthesis of claim 1 wherein the spring member is formed from a plurality of thermoset synthetic resin-impregnated high strength filament sheets molded together as a one piece unit.

4. The prosthesis of claim 3 wherein the filament sheets comprise carbon filaments arranged so they are aligned at angles with the filaments of adjacent sheets.

* * * * *